US 9,488,605 B2

United States Patent
Feser et al.

(10) Patent No.: US 9,488,605 B2
(45) Date of Patent: Nov. 8, 2016

(54) CONFOCAL XRF-CT SYSTEM FOR MINING ANALYSIS

(71) Applicant: Carl Zeiss X-ray Microscopy, Inc., Pleasanton, CA (US)

(72) Inventors: Michael Feser, Orinda, CA (US); Srivatsan Seshadri, San Ramon, CA (US)

(73) Assignee: Carl Zeiss X-ray Microscopy, Inc., Pleasanton, CA (US)

( * ) Notice: Subject to any disclaimer, the term of this patent is extended or adjusted under 35 U.S.C. 154(b) by 185 days.

(21) Appl. No.: 14/020,180

(22) Filed: Sep. 6, 2013

(65) Prior Publication Data

US 2014/0072095 A1    Mar. 13, 2014

Related U.S. Application Data

(60) Provisional application No. 61/698,137, filed on Sep. 7, 2012.

(51) Int. Cl.
| | | |
|---|---|---|
| *G01N 23/00* | (2006.01) | |
| *G01N 23/223* | (2006.01) | |
| *G01N 23/22* | (2006.01) | |
| *G01N 33/24* | (2006.01) | |
| *G01N 23/04* | (2006.01) | |

(52) U.S. Cl.
CPC .......... *G01N 23/223* (2013.01); *G01N 23/046* (2013.01); *G01N 23/2206* (2013.01); *G01N 33/24* (2013.01); *G01N 2223/076* (2013.01); *G01N 2223/419* (2013.01)

(58) Field of Classification Search
CPC ................. G01N 2223/076; G01N 2223/223; G01N 2223/419; G01N 23/046
See application file for complete search history.

(56) References Cited

U.S. PATENT DOCUMENTS

| | | |
|---|---|---|
| 5,192,869 A | 3/1993 | Kumakhov |
| 5,497,008 A | 3/1996 | Kumakhov |
| 5,604,353 A | 2/1997 | Gibson et al. |

(Continued)

FOREIGN PATENT DOCUMENTS

WO    9627194    9/1996

OTHER PUBLICATIONS

International Preliminary Report on Patentability, mailed Mar. 19, 2015, from counterpart International Application No. PCT/US2013/058464, filed Sep. 6, 2013.

(Continued)

*Primary Examiner* — David J Makiya
*Assistant Examiner* — Dani Fox
(74) *Attorney, Agent, or Firm* — HoustonHogle LLP

(57) ABSTRACT

A correlative evaluation of a sample using an x-ray computed tomography (CT) x-ray fluorescence (XRF) system and the method for analyzing a sample using x-ray CT and XRF is disclosed. The CT/XRF system includes an x-ray CT subsystem for acquisition of volume information and a confocal XRF subsystem for acquisition of elemental composition information. The CT/XRF system also includes a controller for managing the acquisitions by the x-ray CT subsystem and confocal XRF subsystem. Combining sub-micrometer spatial resolution 3-D imaging with elemental composition analysis in 3-D with ppm level sensitivity is important to elemental identification of precious metal grains in crushed and ground ores and floatation tailings in the mining industry.

13 Claims, 11 Drawing Sheets

(56) References Cited

U.S. PATENT DOCUMENTS

| | | |
|---|---|---|
| 6,697,454 B1 | 2/2004 | Nicolich et al. |
| 2007/0286339 A1 | 12/2007 | Rothschild |
| 2009/0046832 A1 | 2/2009 | Birnbaum et al. |
| 2011/0188629 A1 | 8/2011 | Meng |
| 2013/0251100 A1 | 9/2013 | Sasaki et al. |
| 2014/0376685 A1 | 12/2014 | Koroteev et al. |

OTHER PUBLICATIONS

Vincze, L. et al., "X-ray Fluorescence Microtomography and Polycapillary Based Confocal Imaging Using Synchrotron Radiation," Developments in X-Ray Tomography IV, Proc. of SPIE vol. 5535, pp. 220-231, 2004.

Schmitz, S. et al., "Chemical U-Th-Pb Dating of Monazite by 3D-Micro X-ray Fluorescence Analysis with Synchrotron Radiation," GFZ, 46 pgs., 2009.

Vekemans, B. "Polycapillary Based Confocal Detection Schemes for Micro and Nano-Spectroscopy," XMI—Department of Analytical Chemistry, Ghent University, Belgium, 30 pgs., 2009.

Markowicz, A. "Activities in the IAEA XRF Laboratory," XRF Newsletter, Issue No. 17, Jul. 2009.

Micro-XRF Analysis for Geological Applications, XRF Application Notes—http://www.horiba.com, 2005.

Fitzgerald, S. "Micro-Spectroscopy-Shedding Light on Rock Formation," http://www.spectroscopyeurope.com, vol. 17:3, pp. 24-25, 2005.

Harmful Element Fluorescence X-Ray Inspection Instrument, http://www.horiba.com, 4 pgs., 2003.

X-Ray Analytical Microscope, http://www.horiba.com, 8 pgs., 2009.

Thermo Scientific Niton XRF Analyzers, http://thermoscientific.com/niton, 10 pgs., 2011.

De Samber, B. et al., "Element-to-Tissue Correlation in Biological Samples Determined by Three-Dimensional X-Ray Imaging Methods," Journal of Analytical Atomic Spectrometry, 2010, 25, pp. 544-553.

Miller, J. D. et al., "Liberation-Limited Grade/Recovery Curves from X-Ray Micro CT Analysis of Feed Material for the Evaluation of Separation Efficiency," International Journal of Mineral Processing, 2009, vol. 93, 48-53.

Scott, D. et al., "High Resolution 3D Tomography for Advanced Package Failure Analysis," Xradia, Inc., 2006, 6 pgs.

Janssens, K. et al., "Minimum Detectable Amounts and Minimum Detection Limits of Normal and confocal u-XRF at Hasylab BL L in Pink Beam Mode," HASYLAB, 2003, 2 pgs.

De Samber, B. et al., "Three-Dimensional Elemental Imaging by Means of Synchrotron Radiation Micro-XRF: Developments and Applications in Environmental chemistry," Anal. Bioanal., Chem., 2008, 390:267-271.

Malzer, "3D Micro X-Ray Fluorescence Analysis," The Rigaku Journal, vol. 23, 2006, pp. 40-47.

Havrilla, G. J. et al., "Confocal X-Ray Fluorescence Microscope Status and Future," HLW Workshop—SRNL, Jan. 19-21, 2005, 28 pgs.

Janssens, K. et al., "Confocal Microscopic X-Ray Fluorescence at teh HASYLAB Microfocus Beamline: Characteristics and Possibilities," Spectrochimica Act, Part B, 2004, vol. 59, pp. 1637-1645.

Woll, A.R. et al. "Development of Confocal X-Ray Fluorescence (XRF) Microscopy at the Cornell High Energy Synchrotron Source," Applied Physics A, 2006, pp. 235-238.

Havrilla, G.J. et al., "Dual-Polycapillary Micro X-Ray Fluorescence Instrument," 51st Annual Denver X-Ray Conf., 2002, 1 pg.

Stock, S.R., Recent Advances in X-Ray Microtomography Applied to Materials, Int. Mater Rev., 2008, vol. 1008:53, pp. 129-181.

Sparks, C.J. et al., "X-Ray Fluorescence Microprobe for Chemical Analysis," Synchrotron Radiation Research, 1980, pp. 459-512.

Partial International Search Report from International Application No. PCT/US2013/058464, mailed on Nov. 25, 2013.

Sasov, A. et al., "A Compact MicroCT/MicroXRF Scanner for Non-Destructive 3D Chemical Analysis," Proceedings on the Conference on Developments in X-Ray Tomography VI, vol. 7078, 70780R, Aug. 28, 2008, 9 pages.

Liu, X. et al., "Calibration of Combined Laboratory MicroCT/MicroXRF System," Proceedings of the Conference of Developments in X-Ray Tomography VIII, vol. 8506, 850615, Aug. 12, 2012, 8 pages.

Boone, M. et al., "3D Petrography of a Cu-Ba Mineralization by Combining muCT and muXRF", Proceedings of the 2011 International Association for Mathematical Geosciences Conference, Sep. 9, 2011, 2 pages.

Miller, J. et al., "Liberation-Limited Grade/Recovery Curves from X-Ray Micro CT Analysis of Feed Material for the Evaluation of Separation Efficiency," International Journal of Mineral Processing, vol. 93, No. 1, Sep. 1, 2009, pp. 48-53.

Patterson, B. et al., "Integrating 3D Images Using Laboratory-Based Micro X-Ray Computed Tomography and Confocal X-Ray Fluorescence Techniques," X-Ray Spectrometry, vol. 39, No. 3, May 1, 2010, pp. 184-190.

International Search Report and Written Opinion of the International Searching Authority mailed Feb. 3, 2014 from counterpart International Application No. PCT/US2013/058464, filed Sep. 6, 2013.

Wang, Y., et al., "A Novel X-ray Microtomography System with High Resolution and Throughput," NSTI-Nanotech, 3:503-507 (2004). Five pages.

Method for acquiring and preparing mineral material for X-ray CT/XRF system analysis

CONFOCAL XRF-CT SYSTEM FOR MINING ANALYSIS

RELATED APPLICATIONS

This application claims the benefit under 35 U.S.C. §119 (e) of U.S. Provisional Application No. 61/698,137, filed on Sep. 7, 2012, which is incorporated herein by reference in its entirety.

BACKGROUND OF THE INVENTION

High-resolution x-ray computed tomography (CT) is a widespread imaging modality with many research and development, as well as industrial, applications. CT systems with three-dimensional (3-D) spatial resolution down to and exceeding one micrometer are available commercially. These systems are widely used for research and find increasing use in industrial applications. See [Scott_2004]-Scott, David et al, A Novel X-ray Micro tomography System with High Resolution and Throughput For Non-Destructive 3D Imaging of Advanced Packages, ISTFA 2004: 30th International Symposium for Testing and Failure Analysis; Boston, Mass.; USA; 14-18 Nov. 2004, 94-98; and [Stock_2008]-Stock, S. R, Recent advances in X-ray microtomography applied to materials, Int. Mater Rev, 1008, 53, 129-181.

X-ray CT has a long track record in integrated circuit (IC) failure analysis. More recently, CT is being used in oil and gas rock analysis to determine porosity and model flow characteristics [Ingrain Digital Rock Physics]. This application has been added to its list of industrial applications. Currently, rapid adoption of high-resolution CT for mining applications is occurring starting with research institutions ([Miller_2009]-Miller, J. D et. al, Liberation-limited grade/recovery curves from X-ray micro CT analysis of feed material for the evaluation of separation efficiency, Int. J. Miner. Process, 2009, 93, 48-53) and has found its way into industrial laboratories with initial focus on tailings analysis for floatation.

Tailings from mining operations are materials left over from processing after most of the valuable minerals have been extracted. Typically, the tailings particles are very small in size—the sizes are of the order of a micrometer to about 100 micrometers ($\mu$m) for platinum and gold operations. Platinum bulk concentrations in tailings are only on the order of 0.5 parts per million (ppm) currently (compared to a few ppms for the raw ore). While the bulk concentrations are very small, the precious metals are not distributed uniformly in the tailings. In fact, they are found in micron sized grains highly localized in space. Left over precious metal is not extracted due to their small particle size, inclusion or association with non-floating minerals, or other inefficiencies of the separation (floatation) process. However, the increasing energy and extraction costs as well as increasingly lower grade of raw ore have created large economic incentives for mining companies to characterize tailings samples better in order to recover precious metals more efficiently through the optimization of separation processes, for example.

Currently, the main scientific instrument used to characterize these tailings is the Mineral Liberation Analyzer (MLA). It is accepted as a standard for accurate mineralogy analysis. The MLA integrates a scanning electron microscope (SEM) with energy dispersive spectroscopy (EDS) having automated sample handling and analysis software dedicated for mineralogy applications.

For tailings analysis, the tailings particles are dispersed and fixed in epoxy such that they are physically separated from each other. These samples are then cut and polished for study under the SEM. First, a back scattered electron (BSE) image of the surface is acquired with high spatial resolution. The signal acquired in the BSE image is proportional to the density and atomic number of the minerals contained in these particles; and the images are depicted with different shades of grey. To accurately determine the mineral composition inside these particles, multiple EDS spectra are obtained and analyses of these spectra provide the basis for determination of minerals.

During the last 10 years, the analysis of tailings with MLA has been attributed with the increased efficiency of extraction of platinum from ore and has led to a decrease of platinum concentration in tailings from ~1 ppm to 0.5 ppm.

SUMMARY OF THE INVENTION

However, the continued study of tailing samples using MLA has multiple problems, chief amongst them are:

1. Tailings from platinum extraction operations typically have the lowest number of particles that actually contain platinum, typically of the order of 0.5 ppm. Thus, multiple samples have to be measured to acquire statistically meaningful data. Often, up to 18 tailing samples ("pucks"), each about 30 millimeters (mm) in diameter, are studied at a time; and this generates only a low statistical data set generally not sufficient to conduct meaningful experimental studies to increase yield.
2. MLA is inherently a two-dimensional (2-D) method and hence only limited information is obtained. This is due to the fact that platinum that is slightly above or below the cut will not be resolved and the 3-D context of the particle remains undetermined. To determine the 3-D context in any statistically significant way, more than 50 cross sectional views of representative particles would typically have to be acquired, which increases the total time to results.
3. Traditional 2-D analysis from SEM has an overestimated mineral recovery [Miller_2009]. Only a complete 3-D analysis can provide an unambiguous solution to the grade recovery curve that is important for determining the operational efficiency of a mining operation.
4. Typical time to results with MLA can be up to 5 days due to the complexity of sample preparation and measurement.

High resolution x-ray CT technology has the potential to overcome all of the problems inherent to MLA mentioned above. The CT technique enables the sampling of a relatively large 3-D volume in a matter of a few hours to locate minerals of interest, such as platinum grains. This enables collection of statistically relevant data with a very short turn-around time allowing for the design of experiments. With the unambiguous, isotropic information content of x-ray CT, true 3-D data of individual particles are collected to completely describe the liberation state of the platinum grains and grain association, which is important for understanding the root cause of yield.

Another type of imaging modality is x-ray fluorescence (XRF). Specifically, confocal XRF was conceived about 20 years ago, but it is only over the past few years that many researchers at various synchrotron facilities have employed confocal set ups. The applications have ranged from elemental imaging in environmental chemistry ([De_Samber_2008]-De Samber, B et al, Three-dimensional elemental imaging by means of synchrotron radiation micro-XRF: developments and applications in environmental chemistry, Anal Bioanal Chem, 2008, 390, 267-271) to the study of composition and structure of ancient paintings ([Malzer_2006]-Malzer, W, 3D Micro X-ray Fluorescence Analysis, The Rigaku Journal, 2006, 23, 40-47) as well as element to tissue correlation in biological samples ([De_Samber_2010]-De Samber, B et. al, Element-to-tissue correlation in biological samples determined by three-dimensional X-ray imaging methods, J. Anal. At. Spectrom., 2010, 25, 544-553). Sensitive trace element detection of transition elements has also been demonstrated ([Janssens_2003] Janssens, K et. al, Minimum Detectable Amounts and Minimum Detection Limits of Normal and Confocal μ-XRF at Hasylab BL L in pink beam mode, HASYLAB Jahresbericht 2002/Schneider J. [edit.], e.a., Hamburg, 2003.). Currently, with the state of the art technology for fabricating polycapillary optics, confocal volume of (~20 μm)$^3$ has already been achieved.

Significant work has been performed in synchrotron facilities to quantify the minimum detection limits and minimum detection amounts of the confocal XRF technique [Janssens_2003, De_Samber_2010]. [Janssens_2003] work has reported sensitivity losses in the confocal setup due to higher air absorption of softer fluorescence x-rays, but confocal XRF had significantly better peak to background ratios for bulk samples compared to conventional XRF, which enabled sub-ppm detection. Some groups have applied their laboratory based confocal XRF setup to probe and analyze paint layers. They reported (10-100 times) worse detection limits than with synchrotron sources albeit with sub optimal setup.

High resolution 3-D x-ray CT has become a widespread imaging modality across many disciplines including materials science, biology, geology, and semiconductors, to name a few. The main shortcoming of x-ray CT is that it produces only "grey scale" images where the intensity of a feature in the image is a proxy for the local mass density (away from x-ray absorption edges).

Thus, in the present invention, x-ray CT is combined with confocal XRF to provide a more complete characterization and understanding of a sample. The detection of 3-D distribution of structures inside the sample is coupled with elemental composition analysis of those structures.

The capability of combining sub-micrometer spatial resolution 3-D imaging with elemental composition analysis in 3-D with ppm level sensitivity is important to many scientific research and industrial applications. A prime industrial example for this is the elemental identification of precious metal grains in crushed and ground ores and floatation tailings in the mining industry. This type of data enables better optimization of extraction yields and leads to improved financial and environmental benefits through the analysis of the 3-D liberation state of the micrometer-sized precious metal grains. The potential applications extend much farther, however. For example, in biological applications, toxicological effects can be related to tissue specific morphology and toxic trace element concentrations.

The present invention, in one example, includes integration of a confocal XRF system into an x-ray CT system as a correlative microscopy solution (CT/XRF). The CT/XRF system has an x-ray CT subsystem, or CT subsystem, and a Confocal XRF subsystem, or CXRF subsystem. When the CT subsystem is acquiring information from the sample, the CT/XRF system is said to be running in CT mode; when the CXRF subsystem is acquiring information from the sample, the CT/XRF system is said to be running in XRF mode.

After performing x-ray CT 3-D imaging of a sample into a CT volume dataset, the CXRF subsystem is preferably used to scan only a limited number of points or small areas predetermined from the structural information of the volume dataset.

This overcomes the main challenge that confocal XRF systems have traditionally faced for widespread adoption, which is the prohibitively long scan times typically required for generating complete 3-D volumes. A key element of the CT/XRF system is exact correlation between the two modalities and the controller/control system that implements this functionality.

In general, according to one aspect, the invention features a correlative evaluation of a sample using a x-ray computed tomography (CT)/x-ray fluorescence (XRF) system including an x-ray CT subsystem for acquisition of volume information, a confocal XRF subsystem for acquisition of elemental composition information; and a controller in communication with the x-ray CT subsystem and the confocal XRF subsystem. The controller coordinates the acquisition by the x-ray CT subsystem and the confocal XRF subsystem.

In one example, the controller provides spatial calibration of the confocal XRF subsystem based on the volume information received from the x-ray CT subsystem.

In general, according to another aspect, the invention features a method for analyzing a sample using x-ray computed tomography and x-ray fluorescence. This method includes the steps of preparing a sample, obtaining a three-dimensional x-ray computed tomography (CT) measurement of the sample, selecting of features of interest in the CT measurement of the sample, defining regions of interest from the selected features of interest, acquiring x-ray fluorescence (XRF) spectra from the defined regions of interest, and matching the acquired XRF spectra with elemental information for identification.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same or similar parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1A:
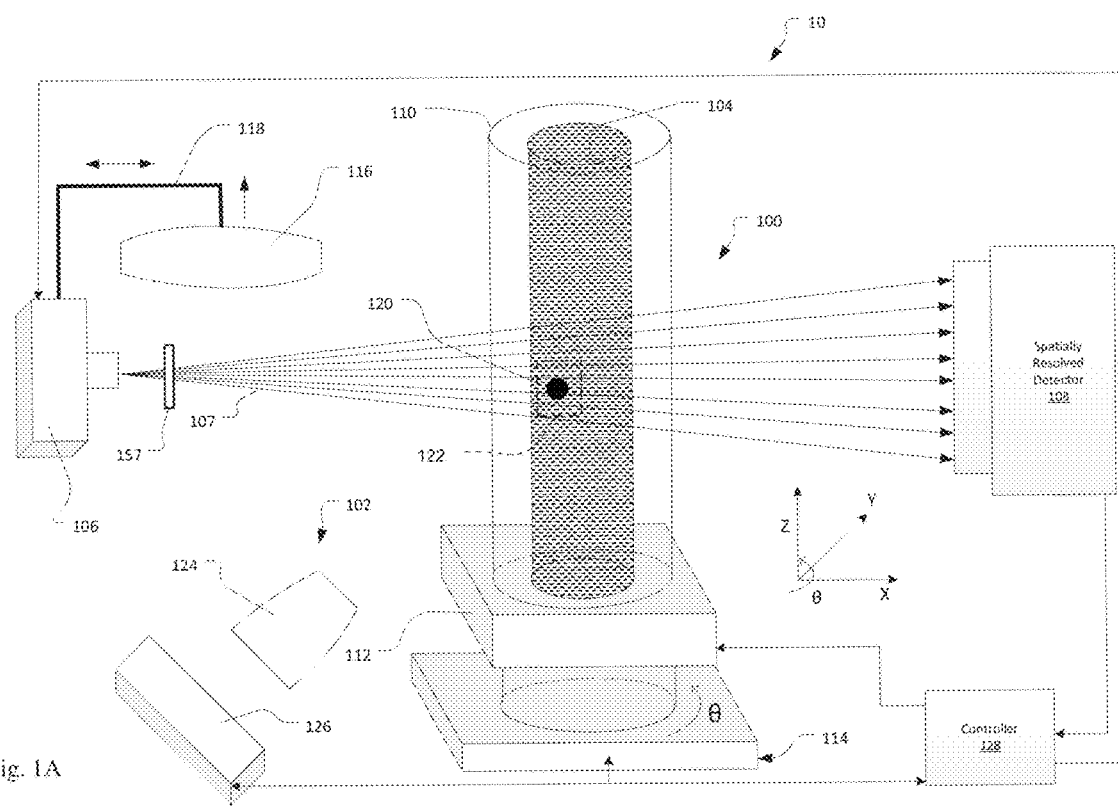
FIG. 1A is a perspective schematic view of an integrated x-ray CT/XRF system in CT mode according to an embodiment of the invention.

3-D images delivered by x-ray CT include a cubic array of voxels with "average" attenuation values. These values are represented by "grey levels". The differences in grey levels, correspond to differences in attenuation and are representative of the material that caused this attenuation. A histogram of these grey level values allows one to analyze and determine the various materials and their phases present in the image, provided the grey levels are suitably calibrated. These grey levels are often sufficient for many applications such as IC failure analysis or porosity analysis for oil and gas rock analysis.

For tailings analysis in mining, ambiguities arise due to so called grey-scale overlaps. These occur if materials with different elemental composition exhibit very similar or same grey levels in the x-ray CT data. For example, if a small high-density grain is found in a tailings sample, it is generally not possible to positively identify this grain as a platinum compound compared to some other high-density compounds (e.g. lead, palladium, etc.). Several hundred known platinum compounds can be present with varying density (and grey scale values) in addition to countless other high-density compounds composed of other elements, making elemental identification extremely important.

The system and method here enables the probing of a grain for elemental composition analysis to give a positive identification to the element and further enables the narrowing of the precise compound. Additionally, in biological applications, the availability of trace-element sensitive spatially resolved probing is useful for toxicological studies to directly put structural changes in context with the presence of toxins.

One of the proposed solutions to some of the problems with the current technology is to complement the x-ray CT scanner with a confocal XRF setup that is able to selectively probe points or small volumes of the x-ray CT volume at a spatial resolution of less than ~(100 um)$^3$ and preferably less than ~(50 um)$^3$, and in some cases less than ~(20 um)$^3$ with ppm level sensitivity.

The ppm sensitivity on bulk homogeneous samples is achieved with confocal XRF. For highly complex and heterogeneous samples as well as samples with very small bulk concentrations where elements to be detected are highly concentrated in very small volumes and localized in space (such as in tailings samples in mining industry), confocal XRF has significant advantages over conventional XRF due to its ability to define the volume of interest to be probed. Confocal XRF also allows for significantly improved signal to background ratios to efficiently detect localized concentrations of elements in thick samples.

One of the chief reasons why the confocal XRF technique has not been commercialized is the non-practicality of scanning large volumes in a reasonable time. Although each point takes only a very short measurement time, usually measured in seconds, a small volume (50×50×50 pixels) can lead to exorbitant measurement times (173 hours for example for a point dwell time of 5 seconds). The key to make confocal XRF practical is to combine it with x-ray CT and only probe a limited number of points in the 3-D volume that are relevant.

This is achieved with the combined CT/XRF system by performing an x-ray CT scan first and then selecting, based on the 3-D structural information, where to collect the elemental information data. As noted earlier, the very small concentrations of platinum are found in micron sized grains highly localized in space and for tailing samples measured in the mining industry only a small number (~10) of grains per x-ray CT scan will be of interest for elemental identification. Such geometry lends itself naturally for the confocal XRF technique and these can be measured by confocal XRF within minutes, adding only minimal time to the CT scan times. This is due to the fact that the grains containing platinum have volumes of the order of $(2\ \mu m)^3$ inside the confocal volumes of the order of $(20\ \mu m)^3$ or about 1000 ppm by volume. This leads to very efficient detection of precious metals which is not possible with conventional XRF.

The same argument holds true for other key applications requiring elemental identification, such as CT grey scale calibration, which generally requires probing only a very limited number of data points in order to correlate grey levels with elemental make-up. For biological applications, it is generally sufficient to probe only within the tissue of the same kind to obtain a representative level of trace elements. For example, in a Zebra fish sample, one would perform measurements within the organs (or a few points within each organ) and not attempt to point-scan the whole specimen.

The coupling of high resolution x-ray CT with confocal XRF helps mitigate and overcome the inherent limitations of the confocal XRF technique on sample sizes. In particular, the coupling overcomes such limitations as limited x-ray penetration into samples and absorption of emergent fluorescence x-rays in the sample. This is because for high resolution x-ray tomography, sample sizes are typically of the order of 1-2 mm. For optimal excitation of platinum (and other precious metals) L fluorescence lines, Mo and Ag sources are, in some embodiments, used with polycapillary optics optimized for MoKα (~17.5 kiloelectron volts (KeV)) and AgKα (~22.2 KeV) radiation, for which the penetration depths inside tailings samples are of the order of ~2 millimeters (mm). For platinum Lα lines (~9.4 KeV) about 10% transmission is expected over ~1 mm which corresponds to a total sample thickness that can be used of ~2 mm (penetration of L x-rays are even larger). For biological applications (for example, tissues), greater x-ray penetration depths (and consequently deeper probing) is achieved, which allows for larger samples to be used. For CT grey scale calibration, exhaustive probing of points deep inside the sample is usually not required. Instead, limited probing of selected points at or near the surface of the specimen is typically sufficient.

FIG. 1A shows an example of the integrated x-ray CT/XRF system 10 in CT mode, which has been constructed according to the principles of the present invention.

This integrated system 10 includes an x-ray CT subsystem 100, or CT subsystem, and a confocal x-ray fluorescence subsystem 102, or CXRF subsystem.

The integrated system 10 also includes a controller 128 that manages various parts of the x-ray CT subsystem 100 and the confocal x-ray fluorescence subsystem 102. The controller 128 receives data from these subsystems 100/102. Based on the data received, the controller 128 manages how these subsystems 100/102 operate accordingly and their operations coordinated.

These subsystems 100/102 are used together to determine the mineral content of a sample 104. Examples of samples 104 include mineral samples such as sandstone, bituminous sand, ore, and coal or samples containing precious metals or fluids, such as water or crude oil.

In the illustrated example, the sample 104 is held within a sample tube 110. This sample tube 110 is a glass or plastic test tube, for example. In one example, the size of the sample is about 1-4 mm in diameter and ~2-20 mm in height.

In another example, the sample is a flat sample that is placed, or not, in a sample container other than the sample tube. Alternatively, the sample 104 can have a different configuration such as cubic or spherical. When flat samples are used, the x, y, z sample stage 112 has the capability to position different regions of the flat face of the samples 104 in x-ray beams 107. The x-ray beams 107 are also referred to as x-ray radiation beams, or simply as x-rays.

The sample tube 110 is mounted on an x, y, z sample stage 112 that allows for the positioning of the sample 104 in the x-ray beam 107 generated by the x-ray source 106. In one example, the x, y, z sample stage 112 comprises three orthogonal motorized positioning arms that allow for the positioning of the sample 104 along each of the three orthogonal dimensions under the control of the controller 128.

The x, y, z sample stage 112 has an integrated rotation stage 114 preferably attached underneath the x, y, z sample stage 112. The integrated rotation stage 114 enables the x, y, z sample stage 112 to rotate through 360 degrees around the vertical (z) axis. This allows the x, y, z sample stage to be rotated along with the sample tube 110 and sample 104 to any desired angle (θ) with respect to the x-ray CT subsystem 100 and/or confocal x-ray fluorescence subsystem 102.

The rotation stage 114 is preferably a precision rotary stage such as an air bearing stage or a mechanical ball-bearing or roller bearing stage.

The x-ray CT subsystem 100 includes an x-ray source 106 that generates the x-ray radiation beam 107. The x-ray source 106 is preferably a laboratory based source such as a sealed tube, rotating-anode, or micro-focus x-ray source. In one example, the x-ray source 106 is a transmission x-ray micro-focus source with a source size of about 2 μm or less operated up to a maximum power of 10 Watts. The small spot size or source size allows for high resolution imaging. Use of a transmission source allows for a favorable imaging geometry by shortening the distance between the source and a detector enabling high throughput.

When the sample 104 is a mineral sample, a high-energy x-ray radiation beam 107 is selected with energy above several keV for the x-ray source 106. This is typically required to penetrate samples with tens of micrometers or greater thickness. Higher energy radiation of tens of keV is used when the sample is usually about a millimeter or greater in thickness. Generally, the range is 5-150 keV. In one embodiment, the x-ray source has a tungsten target.

The x-ray CT subsystem 100 also includes a spatially resolved transmission detector 108. In one example, the detector 108 is a scintillated CCD detector with optical magnification as described in U.S. Pat. No. 7,057,187 B1, which is incorporated herein by this reference in its entirety.

Specifically, the spatially resolved detector 108 records x-ray radiation 107 that passes through the sample 104. In one example, the spatially resolved detector 108 includes a scintillator, a charge-coupled device (CCD) camera, and a lens or lens system for imaging visible light from the scintillator onto the CCD camera.

In CT mode, the x-ray CT subsystem 100 performs sub-micrometer spatial resolution 3-D imaging of the sample 104. The x-ray source 106 emits x-rays 107 that penetrate the sample 104. Then, the x-rays 107 are detected and recorded by the spatially resolved detector 108.

The generated images are passed from the spatially resolved detector 108 to the controller 128. The controller 128 operates the x-ray source 106 and the spatially resolved detector 108 to generate a series of projections 156 of the sample 104. Because the projections 156 are two-dimensional images of the sample 104, projections 156 are also referred to as 2-D projection images. The controller 128 also operates the rotation stage 114. In between projections 156, the controller 128 advances the rotation stage 114 through a predetermined arc. Once enough projections 156 have been generated at different values for θ, the controller 128 combines the images or projections 156 into a 3-D tomographic image of the sample 104.

In one example, a series of 2-D projection images (typically about 1600 images or more) are obtained and mathematically reconstructed to produce a 3-D volume, with grey value in each voxel representing the optical density. The conditions of acquisition of images are optimized for speed and maximization of signal to noise ratios.

Source filters 157 are used in some examples, to preharden the x-ray beam 107 incident on the sample 104 to ensure proper beam hardening corrections to the reconstructed data. Suitable calibration can be performed and CT numbers obtained in terms of Hounsfield Units which gives a measure of linear attenuation coefficient in the material at a given location.

Figure 1B:
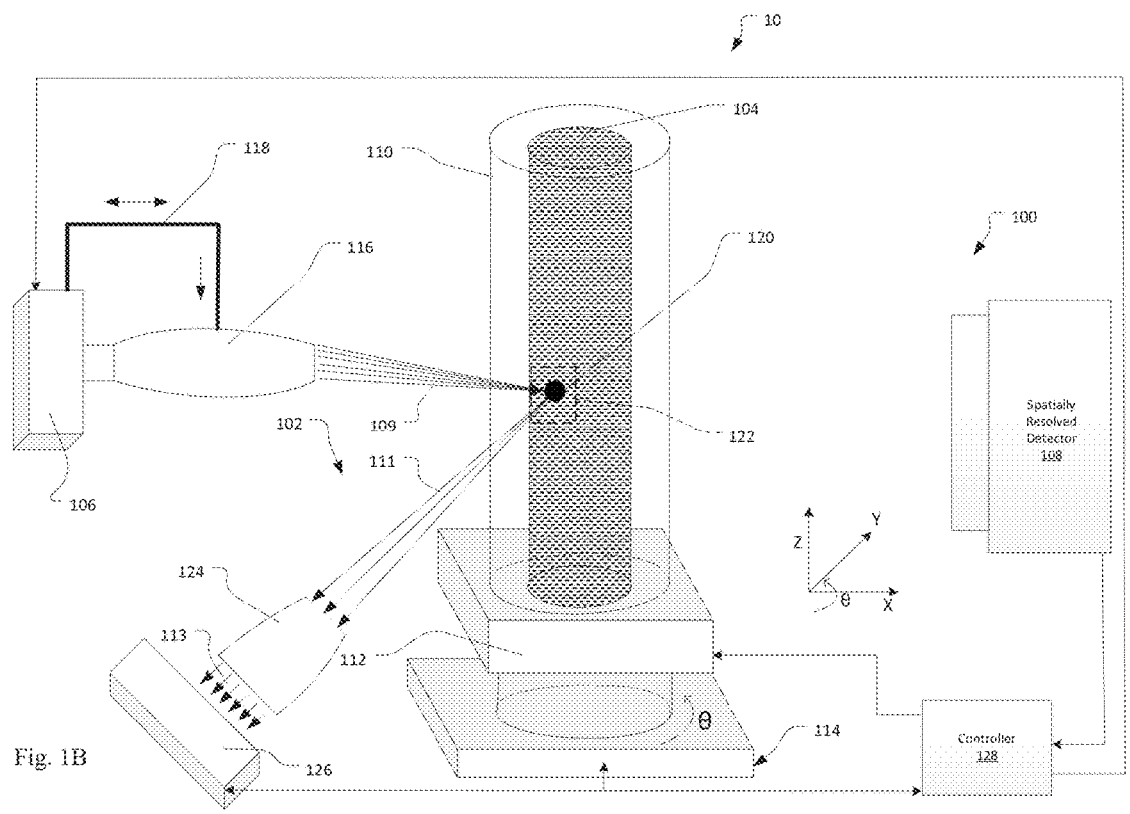
FIG. 1B is a perspective schematic view of the integrated x-ray CT/XRF system from FIG. 1A in XRF mode.

In one embodiment, the controller 128 commands the switching of the x-ray source 106 from CT mode to XRF mode and back to CT mode. This can be accomplished with a switchable source optical element 116 such as an elliptical polycapillary optic. In one example, the switchable source optical element 116 is attached to the x-ray source 106 via a moveable arm 118. When the controller 128 directs the x-ray source 106 to switch to XRF mode, the switchable source optical element 116 is positioned into the path of the x-rays 107 and in front of the x-ray source 106 as shown in FIG. 1B. When the controller 128 directs the x-ray source 106 to switch back to CT mode, the switchable source optical element 116 detaches from the x-ray source 106 and is moved out of the path of the x-rays 107 as shown in FIG. 1A.

FIG. 1B shows an example of the integrated x-ray CT/XRF system 10 in XRF mode.

During XRF mode, the source optical element 116 functions to control and direct x rays over a broad range of angles and energies from the source to generate a small focused x-ray beam 109 onto a volume or region of interest 122 in the sample 104.

The confocal x-ray fluorescence subsystem 102 further includes a collection optical element 124 and an x-ray fluorescence detector 126.

The collection optical element 124 is preferably a half optic that can be used to minimize the total number of reflections of x-rays inside the optical element 124. In another example, the collection optical element 124 is an elliptical polycapillary optic. The collection optical element 124 gathers fluorescence x-rays 111 that are generated within the particular region of interest 122.

The intersection of the foci of source optical element 116 and the collection optical element 124 defines the confocal volume which depends on the focus size and strongly depends upon the detected fluorescence x-ray energy. The confocal volume, as defined by the intersection of the foci of source optical polycapillary element 116 and the collection optical polycapillary element 124, is approximately (50 µm)$^3$ in one example or (20 µm)$^3$ in another example. In a current embodiment, the source optical element 116 is optimized for AgKa (~22.2 KeV) characteristic x-rays from the source 106. On the detection side, the half optic collection optical element 124 is used to minimize the total number of reflections of x-rays inside the capillaries and increase efficiency of detection of fluorescence x-rays from the sample.

In general, the collection optical element 124 is optimized to detect fluorescence x-rays in the energy range of 9-13 KeV (suitable for detection of precious metals) most efficiently. For examples where mid Z transition elements have to be efficiently detected, the collection optical element 124 is suitably optimized for the K lines of these elements whose energies lie in the 7-10 KeV range. The length of the collection optical element 124 is optimized and the distance between the energy dispersive x-ray fluorescence detector 126 and the sample surface is minimized to reduce the absorption of softer fluorescence x-rays in air such that the sensitivity of the instrument is not severely compromised.

The collection optical element 124 accepts emitted fluorescence x-rays 111, and produces, or collimates the emitted fluorescence x-rays 111 into, a parallel beam of fluorescence x-rays 113 onto the x-ray fluorescence detector 126. The x-ray fluorescence detector 126 is an energy-dispersive x-ray spectroscopy (EDS) detector, in one example. The EDS detector converts the x-ray energy received from the collimated fluorescence x-rays 113 into voltage signals. Based on the voltage signals (characterizing x-ray energy), an elemental composition of the region of interest 122 is determined. In one example, the Lα and Lβ lines of platinum (9.45 KeV and 11.2 KeV) and lead (10.45 KeV and 12.62 KeV) are used to identify and distinguish between the two metals in the sample 104.

The controller 128 is in communication with the confocal x-ray fluorescence subsystem 102. Based on the results of the CT analysis in FIG. 1A, the controller 128 selects subsequent regions of interest 122 from the volume information to be probed by the x-ray fluorescence subsystem 102. In more detail, the controller 128 operates the x, y, z sample stage 112/rotation stage 114 to rotate around the z-axis and position the sample tube 110 along the x, y, and z axes in relation to the confocal x-ray fluorescence subsystem 102. This provides desired positioning of the region of interest 122 with respect to the x-ray source 106 and the collection optical element 124/x-ray fluorescence detector 126. The rotation/positioning is optimized to reduce absorption of fluorescent x-rays.

In XRF mode, the confocal x-ray fluorescence subsystem 102 performs elemental composition analysis of the sample 104. The x-ray source 106 emits x-rays 109 through the switchable source optical element 116 which focuses or directs the x-rays 109 towards an analysis region or a region of interest 122 in the sample 104. Typically, the x-rays 109 used for CT mode will not be optimal for the XRF mode. Thus, in one example, the source 106 uses a new Ag target that can be operated at greater than the energy used in CT mode, such as greater than 20 Watts or up to 50 Watts or more.

In general, in this and the subsequent embodiments, the CT imaging subsystem 100 typically uses an x-ray source 106 with a high Z target, such as tungsten (W) which generates comparatively broadband radiation. In contrast, the XRF subsystem 102 typically uses lower Z x-ray source targets such as molybdenum, rhodium, and silver that produce a more single energy x-ray beam. Generally, CT sources use targets in which Z>50 and produce greater than 50% of the beam energy in the continuum. In contrast, XRF subsystems use targets in which Z<50, where greater than 50% of the energy of the x-ray beam is in the characteristic lines.

The focused x-rays 109 induce fluorescence of elements within the analysis region 122, which are collected by the collection optical element 124. The collection optical element 124 receives emitted fluorescence x-rays 111. Then, the collection optical element 124 collimates the emitted fluorescence x-rays 111 into collimated fluorescence x-rays 113. The collimated fluorescence x-rays 113 are targeted towards an x-ray fluorescence detector 126 for detecting the x-rays 111/113 from the region of interest 122.

The controller 128 receives data regarding elemental composition information of the region of interest 122 from the x-ray fluorescence detector 126 in the form of energy spectra. These data are converted by the controller 128 into a map of the elemental composition of the sample 104 for each of the regions of interest 122 that is analyzed.

Figure 2:
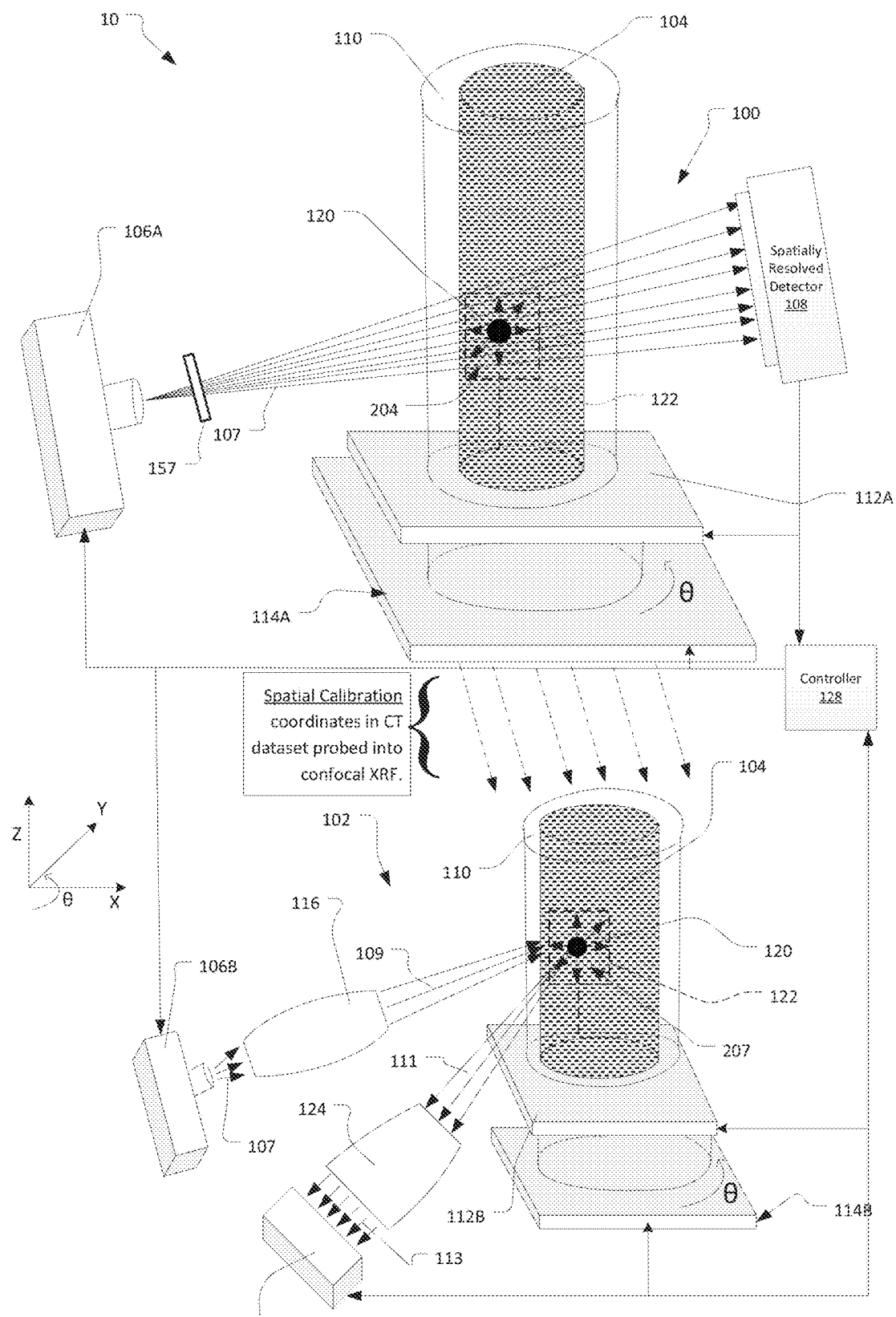
FIG. 2 is a perspective schematic view of an x-ray CT/XRF system including a separate x-ray CT subsystem and a separate confocal XRF subsystem that function together according to another embodiment of the invention.

In FIG. 2, the CT/XRF system 10 is shown as two separate subsystems. CT mode or function is performed using an x-ray CT subsystem 100. Then, the sample tube 110 is transferred to a separate confocal XRF subsystem 102. These separate subsystems are used in combination to determine the mineral content, for example, of the sample 104 within the sample tube 110.

This CT/XRF system 10 includes a controller 128 that manages various parts of the x-ray CT subsystem 100 and the confocal x-ray fluorescence (CXRF) subsystem 102. The controller 128 receives data from these subsystems 100/102. Based on the data received, the controller manages how these subsystems 100/102 operate.

Typically, the sample tube 110 is first mounted on an x, y, z sample stage 112A of the x-ray CT subsystem 100. As described above, this x, y, z sample stage 112A has an integrated rotation stage 114A for rotating the sample tube 110 to any desired angle (θ) with respect to the x-ray CT subsystem 100. The x-ray CT subsystem 100 includes a first x-ray source 106A and a spatially resolved transmission detector 108.

During CT mode, the CT subsystem 100 is activated to collect a series of projections 156 at different values for θ. The projections 156 are combined into a 3-D tomographic reconstruction 150 of the sample 104.

Specifically, the first x-ray source 106A emits diverging x-rays 107 through the features of interest 120. In one example, the x-ray source 106A is a transmission x-ray micro source with source size of about 2 µm or less and preferably 1.5 µm or less operated up to a maximum power of 10 Watts. In another example, the x-ray source 106A is a reflection source having a source size or spot size of about 5 µm or less operated at a power between about 10 and 30 Watts. These x-rays 107 are captured and recorded by the spatially resolved detector 108. The spatially resolved detector 108 generates images from the detection of these x-rays 107. These images are passed to the controller 128 to develop 3-D tomographic images 150 of the sample 104. As described previously, the controller 128 operates the x-ray source 106A along with the integrated rotation stage 114A to obtain the projections 156 for the different values of θ.

Next, the CT/XRF system 10 switches from CT mode to XRF mode. The sample 104 is switched from the x, y, z sample stage 112A of the CT system 100 to the x, y, z sample stage 112B of the XRF system 102. A compatible kinematic mounting system is used for both systems 100, 102 to enable reproducible sample transfer that keeps a fixed coordinate transformation between both systems.

During the switch, the controller 128 provides spatial calibration of the confocal XRF subsystem 102 based on the results of CT mode. Spatial calibration is the transfer of system coordinates (x, y, z, θ) from the x-ray CT subsystem 100 to the confocal x-ray fluorescence subsystem 102. The controller 128 receives CT system coordinates 204 (x, y, z, θ)$_{CT}$ from the x-ray CT subsystem 100 that characterize the locations of the features of interest 120. The CT system coordinates 204 (x, y, z, θ)$_{CT}$ are converted by the controller 128 to XRF system coordinates 207 (x, y, z, θ)$_{XRF}$. This conversion defines a region of interest 122 for the confocal XRF subsystem 102.

The confocal XRF subsystem 102 includes a second x-ray source 106B in communication with the controller 128. The controller 128 adjusts this second x-ray source 106B accordingly during XRF mode. In one example, the second x-ray source 106B is a laboratory micro focus source with Ag target that is operated at greater than 20 Watts or 50 Watts or more. Generally, however, the source's target as a Z of less than 50, as discussed previously.

The confocal XRF subsystem 102 also has a second rotation stage 114B and a second x, y, z sample stage 112B for receiving and holding the sample tube 110 from the x-ray CT subsystem 100. The controller 128 directs the rotation of the sample tube 110 via the second x, y, z sample stage 112B/rotation stage 114B based on the XRF system coordinates 207.

The confocal XRF subsystem 102 includes the source optical element 116 such as an elliptical polycapillary optic for focusing the x-rays 109. The source optical element 116 can be attached to the second x-ray source 106B or placed in front of the second x-ray source 106B.

The confocal XRF subsystem 102 is able to collect fluorescence radiation with the collection optical element 124 and detect that radiation with the x-ray fluorescence detector 126 as described above.

In XRF mode, the separate confocal x-ray fluorescence subsystem 102 performs elemental composition analysis of the sample 104, which is typically limited to regions of interest 122 identified in the CT analysis. The second x-ray source 106B emits x-rays 107 through the source optical element 116 which focuses the x-rays 109 towards a region of interest 122 in the sample 104. In the illustrated example, the controller operates the rotation stage 114B and the x, y, z sample stage 112B of the XRF subsystem 102 to place the desired regions of interest 122 at the focal point of the source optical element 116 and the collection optical element 124. The focused x-rays 109 induce fluorescence of elements within the region of interest 122. Fluorescence x-rays 111 are received and guided by the collection optical element 124 towards an x-ray fluorescence detector 126 for detecting the fluorescence x-rays 111/113 from the region or volume of interest 122.

The controller 128 receives data regarding energy of the x-rays detected by the fluorescence detector 126 and thus the elemental composition information of the region of interest 122. These data are converted by the controller 128 into a map of the elemental composition within the analyzed regions of interest 122.

Figure 3:
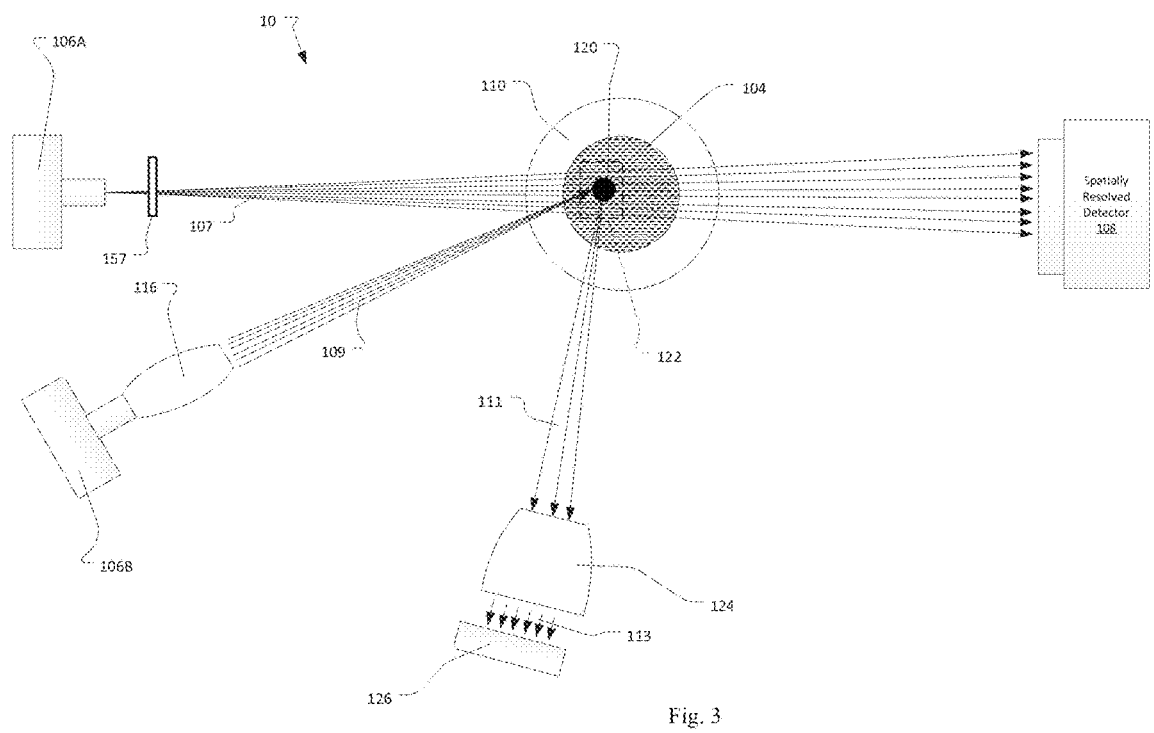
FIG. 3 is a top schematic view of an integrated x-ray CT/XRF system running both the CT mode and the XRF mode simultaneously or serially according to another embodiment of the invention.

FIG. 3 illustrates another example of a CT/XRF system 10. This is a top view of an integrated CT/XRF system 10 that has the capability of running both CT analysis and XRF analysis simultaneously or sequentially without removing the sample from the system.

In this example, two x-ray sources 106A/106B are used. The first x-ray source 106A is for CT analysis. The second x-ray source 106B includes an optical element 116 attachment for XRF analysis.

In simultaneous CT/XRF mode, the first x-ray source 106A emits a dispersive group of x-rays 107 across features of interest 120 in the sample 104. The second x-ray source 106B utilizes the source optical element 116 to emit a focused set of x-rays 109 at a region of interest 122 in the sample 104.

The CT/XRF system 10 can simultaneously develop 3-D CT images as well as XRF elemental composition images during CT/XRF mode. The x-rays 107 are captured and detected by the spatially resolved detector 108. The focused x-rays 109 are collected and guided by the collection optical element 124. The collection optical element 124 captures the fluorescence x-rays 111 and directs the rays 113 as a parallel beam towards an x-ray fluorescence detector 126 for detecting the fluorescence rays 111/113 from the region of interest 122.

The CT/XRF system 10 can alternatively run CT mode or XRF mode at different times from one another. For example, the CT/XRF system 10 is run in CT mode first to determine desired features of interest 120 in the sample 104. Then, the system 10 is run in XRF mode to analyze the regions of interest 122 that surround the desired features of interest 120 to thereby determine the elemental composition.

Figure 4:
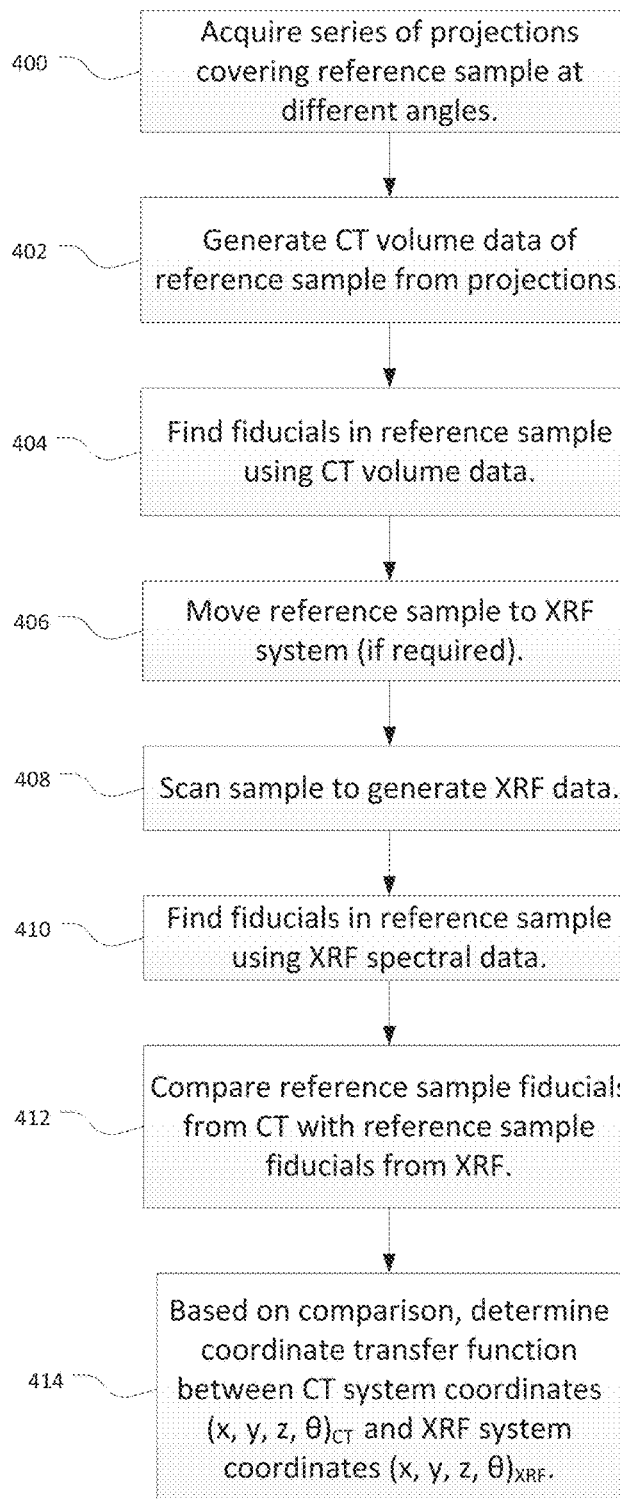
FIG. 4 is a flowchart illustrating an x-ray CT/XRF system calibration method according to an embodiment of the invention.

FIG. 4 illustrates an example of the steps for a calibration process of a CT/XRF system according to an embodiment of the invention.

In step 400, a series of projections are acquired covering the reference sample at different angles. In one example, the reference sample includes at least three fiducial markers, also known as fiducials, in three different planes. This is required for unambiguous coordinate transfer. Preferably, the fiducial markers have high contrast in CT mode and are identifiable in XRF mode. In one example, high density spheres, such as 1-10 µm diameter copper or gold spheres, function as fiducials. These fiducials are embedded in an epoxy matrix plug that functions as the reference sample. In another example, a cross-shaped fiducial is deposited on a membrane, that functions as the reference sample or target.

Then, in step 402, CT volume data of the reference sample is generated from the projections. Next, in step 404, the one or more fiducials are found in the reference sample using the CT volume data.

Depending on the type of CT/XRF system, the reference sample may need to be moved to the XRF system in step 406, using a common kinematic mounting system. In step 408, the sample is scanned to generate XRF data. In step 410, fiducials are found in the reference sample using the XRF spectral data. The reference sample fiducials from the CT are compared with the reference sample fiducials of the XRF in step 412. In step 414, based on the step 412 comparison, a coordinate transfer function is determined between CT system coordinates (x, y, z, $\theta$)$_{CT}$ and XRF system coordinates (x, y, z, $\theta$)$_{XRF}$.

Before a mineral sample 104 is placed into a sample tube 110 for analysis by the CT/XRF system 10, a pack of mineral material needs to be acquired and prepared.

Figure 5:
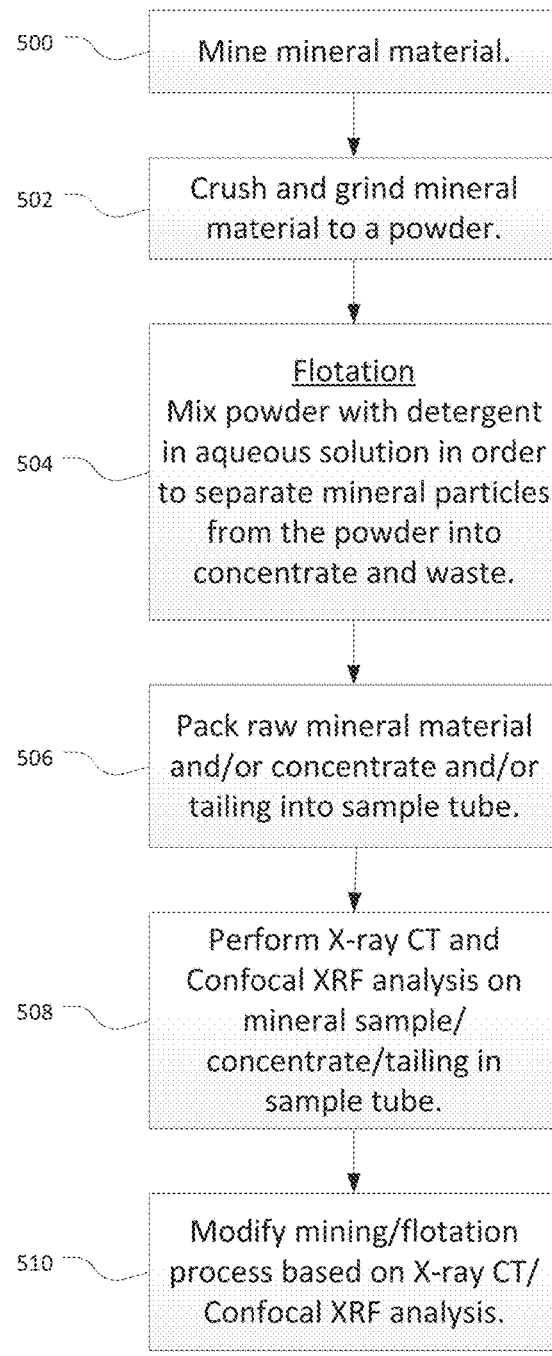
FIG. 5 is a flowchart illustrating a method for acquiring and preparing a mineral material for x-ray CT/XRF analysis according to an embodiment of the invention.

FIG. 5 illustrates an example of the steps involved in converting mineral material to a mineral sample for analysis.

In step 500, mineral material is mined. Then, in step 502, the mineral material is crushed and ground into a powder. This mineral powder is run through a flotation process in step 504. Flotation includes mixing the powder with detergent in an aqueous solution in order to separate mineral particles from the powder into the concentrate and tailings. Next, in step 506, the raw mineral material and/or concentrate and/or tailings are packed into a sample tube 110.

In step 508, x-ray CT and confocal XRF analysis are performed on this mineral sample/concentrate/tailing 104 in the sample tube 110. Based on the results of the x-ray CT/confocal XRF analysis, the mining/flotation process is modified and/or optimized in step 510.

Figure 6A:
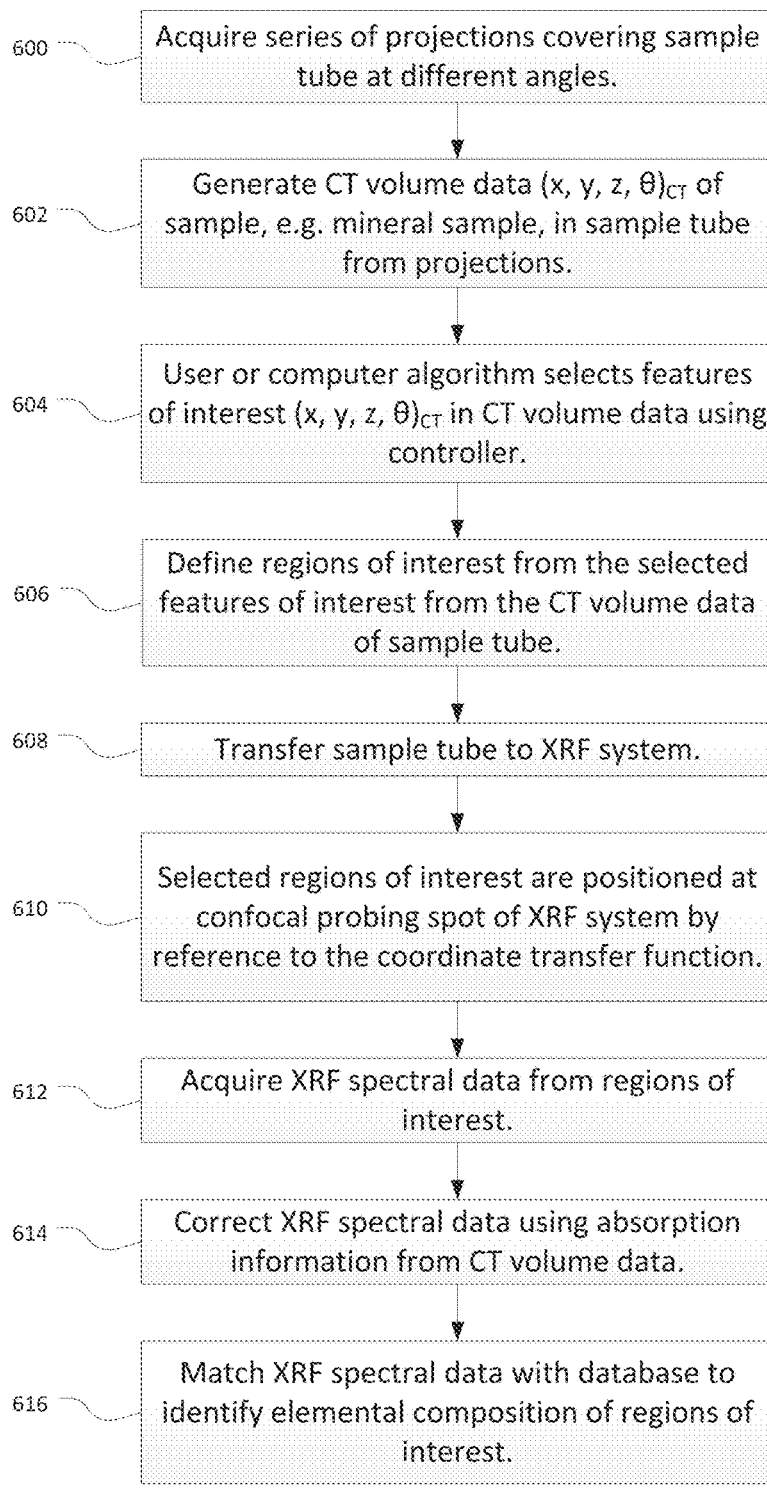
FIG. 6A is a flowchart illustrating a method of analyzing a sample using separate x-ray CT and Confocal XRF subsystems according to an embodiment of the invention.
Figure 6B:
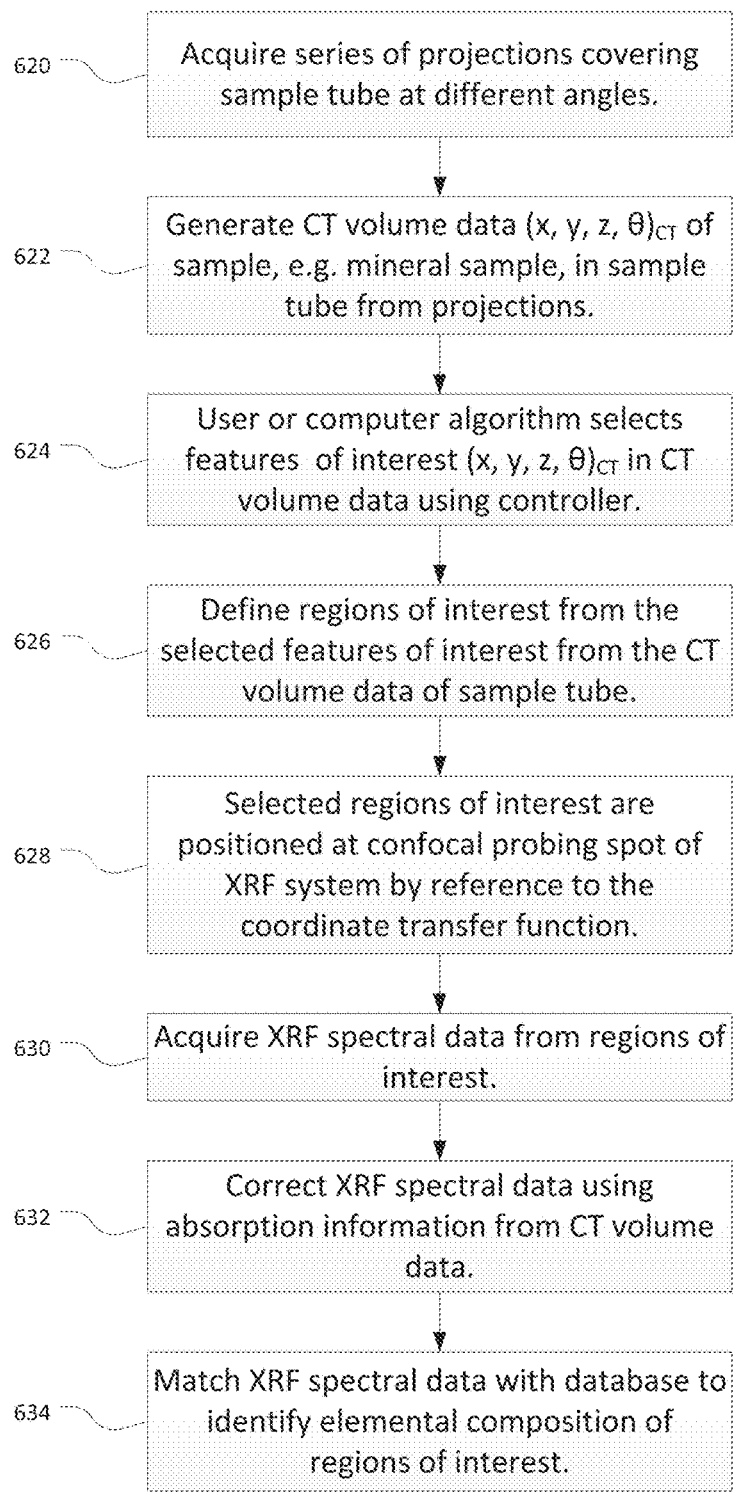
FIG. 6B is a flowchart illustrating a method of analyzing a sample using an integrated x-ray CT/XRF system according to an embodiment of the invention.

The analysis of a sample using a CT/XRF system is a process that can be run through separate CT and XRF systems or an integrated CT/XRF system as illustrated in FIGS. 6A and 6B.

This process starts with a step 600/620 of acquiring a series of projections covering the sample 104 within the sample tube 110 at different angles. In step 602/622, CT volume data (x, y, z, $\theta$)$_{CT}$ of the sample (e.g. mineral sample) are generated from the projections. This is accomplished using tomographic reconstruction algorithms that are executed by the controller 128, for example.

Next, in step 604/624, a user or computer algorithm executing on the controller 128 selects features of interest (x, y, z, $\theta$)$_{CT}$ in the CT volume data.

In steps 606/626, regions or volumes of interest are defined from the selected features of interest based on the CT volume data of the sample. In general, the resolution of the CT volume data is a few microns, or less. In contrast, the resolution limit of the XRF system under current technologies is ~(20 µm)$^3$. Thus, for each feature of interest that is identified in the CT volume data, a region of interest surrounding that feature is defined for the analysis executed by the XRF system.

If the analysis is performed using separate CT and XRF systems, step 608 includes the transfer of a sample tube to the XRF system after the regions of interest are defined. In step 610/628, the selected regions of interest are positioned at the confocal probing spot of the XRF system by reference to the coordinate transfer function. In step 612/630, XRF spectral data from the regions of interest are acquired. The XRF spectral data are corrected using absorption information from the CT volume data in step 614/632. Then, in step 616/634, the XRF spectral data are matched with a database of information that correlates with elemental composition. Based on this match, the controller is able to identify the elemental composition of the regions of interest.

Figure 7A:
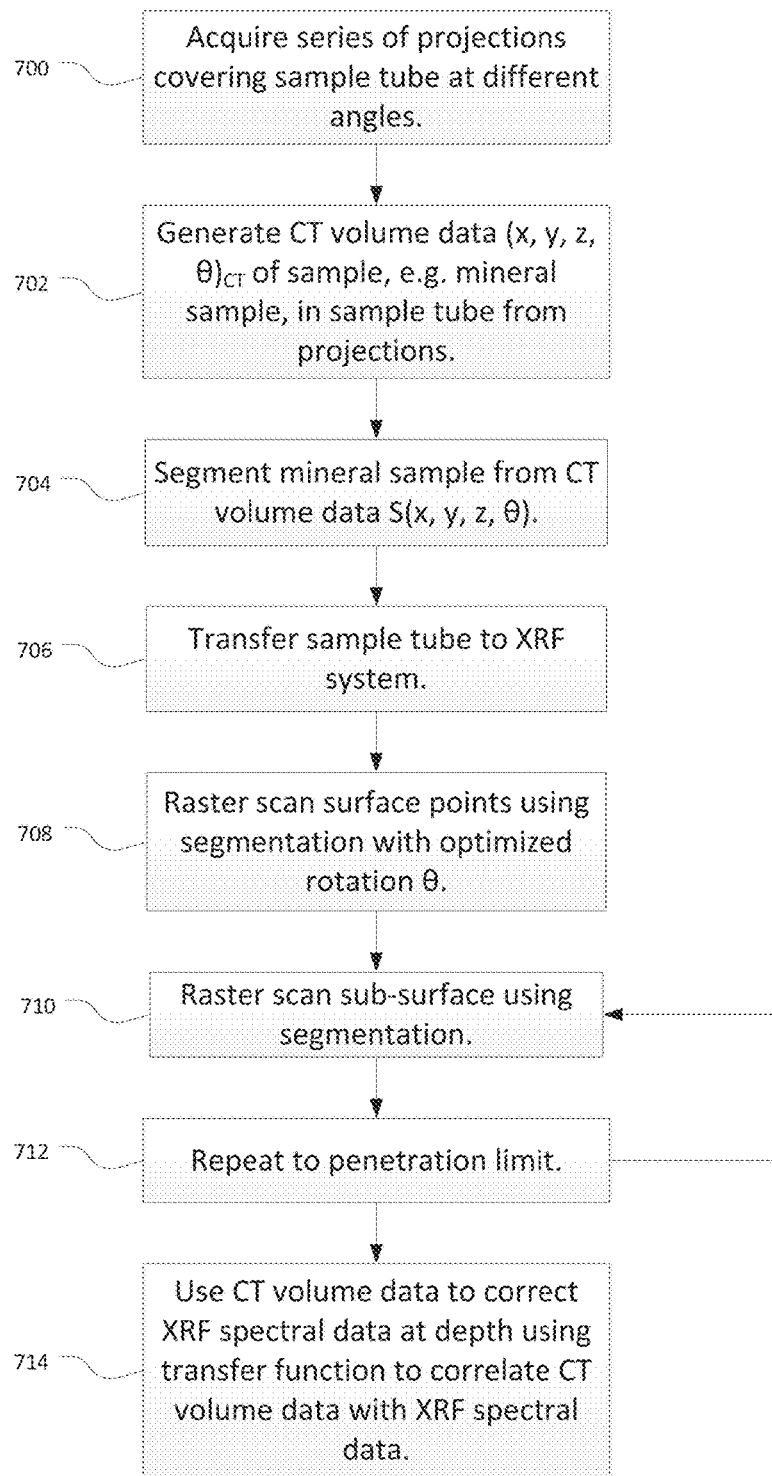
FIG. 7A is a flowchart illustrating a raster scan analysis of a sample using separate x-ray CT and Confocal XRF subsystems according to an embodiment of the invention.
Figure 7B:
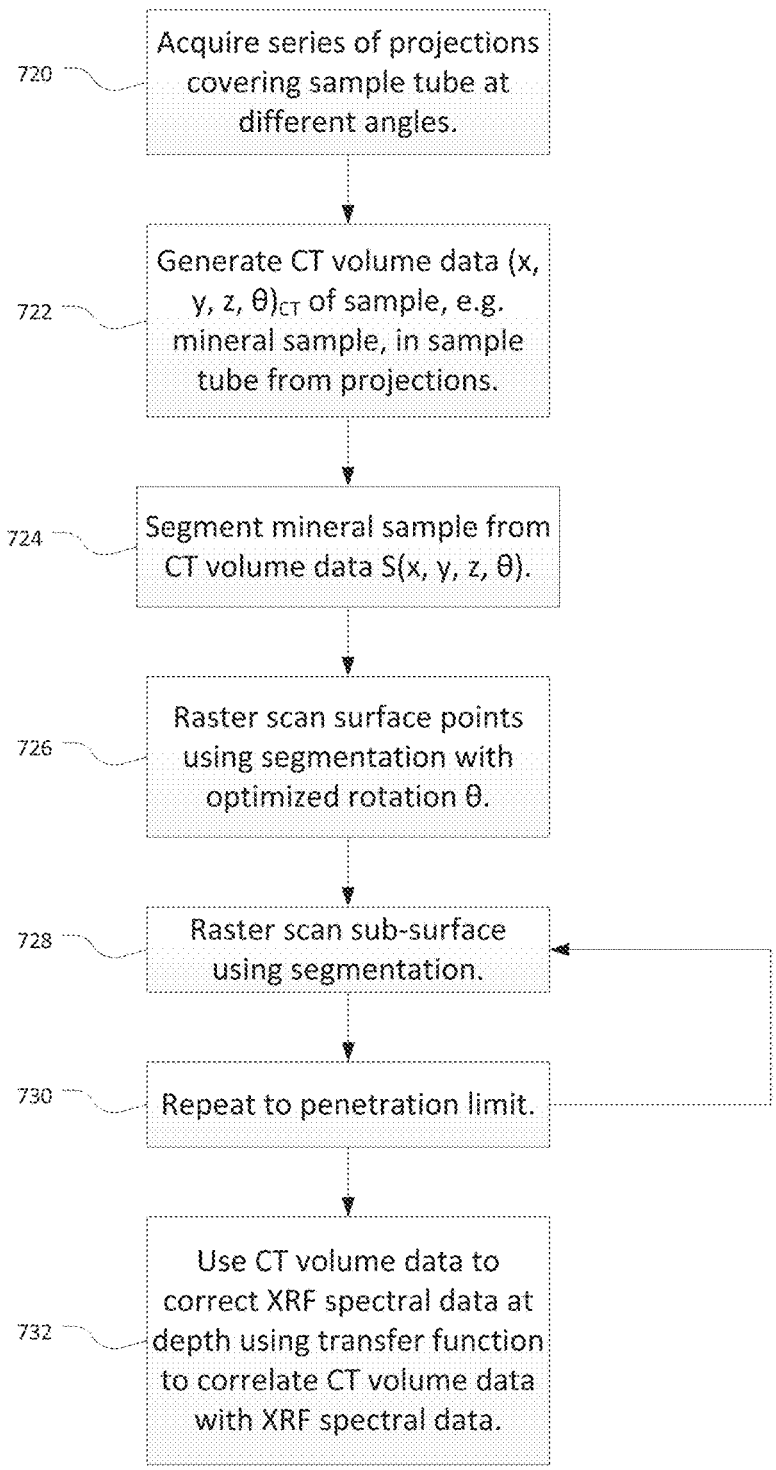
FIG. 7B is a flowchart illustrating a raster scan analysis of a sample using an integrated x-ray CT/XRF system according to an embodiment of the invention.

A raster scan analysis of the sample with a CT/XRF system can also be performed using separate CT and XRF systems or an integrated CT/XRF system as illustrated in FIGS. 7A and 7B.

This process starts with step 700/720 of acquiring a series of projections covering the sample 104 within the sample tube 110 at different angles.

In step 702/722, CT volume data (x, y, z, $\theta$)$_{CT}$ of the sample (e.g. mineral sample) is generated from the projections. The sample is segmented from the CT volume data S(x, y, z, $\theta$) in step 704/724. If the analysis is using separate CT and XRF systems, in step 706 the sample tube 110 is transferred to the XRF system after the sample is segmented in step 704. Next, in step 708/726 surface points are raster scanned using segmentation with optimized rotation $\theta$. The sub-surface of the sample is raster scanned using segmentation in step 710/728. In step 712/730, the raster scan sub-surface step 710/728 is repeated to penetration limit.

The CT volume data are used to correct the XRF spectral data at depth using the transfer function to correlate CT volume data with XRF spectral data in step 714/732.

Figure 8:
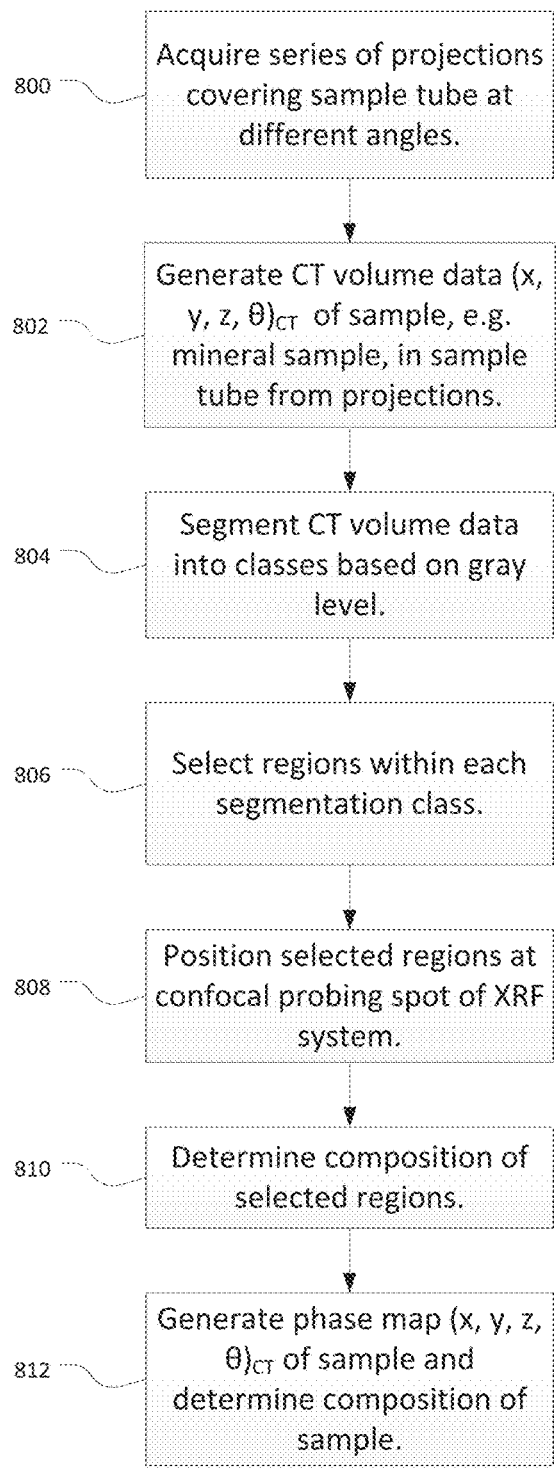
FIG. 8 is a flowchart illustrating a method of determining the composition of a sample using an x-ray CT/XRF system according to an embodiment of the invention.

FIG. 8 illustrates the process of determining the composition of the sample using CT and XRF systems.

In step 800, the process starts with acquiring a series of projections covering the sample 104 within the sample tube 110 at different angles. CT volume data (x, y, z, $\theta$)$_{CT}$ of the sample (e.g. mineral sample) is generated from the projections in step 802. Next, in step 804, the CT volume data are segmented into classes based on gray level. In step 806, regions within each segmentation class are selected. Selected regions are positioned at the confocal probing spot of the XRF system in step 808. In step 810, the composition of the selected regions is determined. Then, in step 812, a phase map (x, y, z, $\theta$)$_{CT}$ of the sample is generated and the composition of the sample is determined using the composition information that is generated for each gray level in the CT volume data.

While this invention has been particularly shown and described with references to preferred embodiments thereof, it will be understood by those skilled in the art that various changes in form and details may be made therein without departing from the scope of the invention encompassed by the appended claims.

What is claimed is:

1. An x-ray computed tomography (CT)/x-ray fluorescence (XRF) system comprising:
    an x-ray CT subsystem for acquisition of volume information;
    a confocal XRF subsystem for acquisition of elemental composition information; and
    a controller in communication with the x-ray CT subsystem and the XRF confocal subsystem, wherein the controller manages the acquisition by the x-ray CT subsystem and the confocal XRF subsystem, enables the identification and selection of a feature of interest within the volume information acquired by the x-ray CT subsystem, generates a coordinate transfer function for translating the selected feature of interest from the volume information of the x-ray CT subsystem, and uses the generated coordinate transfer function to define a region of interest for subsequent acquisition of the elemental composition information the confocal XRF subsystem from the selected feature of interest.

2. The system of claim 1, wherein the controller provides spatial calibration of the confocal XRF subsystem based on the volume information received from the x-ray CT subsystem.

3. The system of claim 1, wherein the controller combines the volume information from the x-ray CT subsystem with the elemental composition information from the confocal XRF subsystem to verify liberation states of elements within the sample.

4. The system of claim 1, wherein the controller selects a number of points or areas predetermined from the volume information for the acquisition of the elemental composition information by the confocal XRF subsystem.

5. The system of claim 1, wherein the controller:
   selects a region of interest that includes the feature of interest; and
   accesses the region of interest with the confocal XRF subsystem for the acquisition of the elemental composition information.

6. The system of claim 1, wherein the confocal XRF subsystem positions the region of interest at a confocal probing spot of the confocal XRF subsystem by referencing the coordinate transfer function.

7. The system of claim 1, wherein the controller corrects the elemental composition information acquired by the confocal XRF subsystem using absorption information of the volume information acquired by the x-ray CT subsystem.

8. The system of claim 1, wherein the controller compares the elemental composition information acquired by the confocal XRF subsystem against a database of information for identification.

9. The system of claim 1, wherein the confocal XRF subsystem comprises:
   a source optical element for directing x rays received over a range of angles to generate a focused x-ray beam in regions of interest of the sample; and
   a collection optical element that gathers x-rays generated within the regions of interest in the sample for detection by a detector.

10. A method for analyzing a sample using x-ray computed tomography and x-ray fluorescence, the method comprising:
   obtaining a three-dimensional x-ray computed tomography (CT) measurement of a sample;
   selecting of features of interest in the CT measurement of the sample;
   defining regions of interest from the selected features of interest;
   generating a coordinate transfer function to translate the selected features of interest to thereafter acquire x-ray fluorescence (XRF) spectra from the defined regions of interest with a confocal system; and
   matching the acquired XRF spectra with a database of information for identification.

11. The method of claim 10, further comprising combining the three-dimensional x-ray CT measurement of the sample with the identification of elements within the sample to verify a liberation state of elements within the sample.

12. The method of claim 10, further comprising selecting a number of points or areas predetermined from the x-ray CT measurement of the sample for the acquisition of the XRF spectra.

13. The method of claim 10, wherein the acquiring the XRF spectra from the defined regions of interest comprises using a collection optical element that gathers x-rays generated within the regions of interest in the sample.

* * * * *